(12) United States Patent
Arvanitakis

(10) Patent No.: US 10,968,418 B1
(45) Date of Patent: Apr. 6, 2021

(54) COMPOSITIONS FOR MAINTAINING CLEAN SURFACES AND METHODS FOR MAKING AND USING CLEAN SURFACE TECHNOLOGY

(71) Applicant: Nicholas Joseph Wilson Arvanitakis, Cochise, AZ (US)

(72) Inventor: Nicholas Joseph Wilson Arvanitakis, Cochise, AZ (US)

(73) Assignee: Group Holdings, LLC, Sioux Falls, SD (US)

( * ) Notice: Subject to any disclaimer, the term of this patent is extended or adjusted under 35 U.S.C. 154(b) by 0 days.

(21) Appl. No.: 16/174,186

(22) Filed: Oct. 29, 2018

Related U.S. Application Data

(60) Provisional application No. 62/577,930, filed on Oct. 27, 2017.

(51) Int. Cl.
| | |
|---|---|
| *C11D 11/00* | (2006.01) |
| *C11D 7/32* | (2006.01) |
| *C11D 7/20* | (2006.01) |
| *C11D 7/26* | (2006.01) |
| *C11D 17/00* | (2006.01) |
| *A61L 2/00* | (2006.01) |

(52) U.S. Cl.
CPC .............. *C11D 7/3209* (2013.01); *A61L 2/00* (2013.01); *C11D 7/20* (2013.01); *C11D 7/26* (2013.01); *C11D 7/265* (2013.01); *C11D 11/0023* (2013.01); *C11D 11/0094* (2013.01); *C11D 17/0008* (2013.01); *A61L 2202/17* (2013.01)

(58) Field of Classification Search
CPC .............................. C09G 1/00; C11D 11/0035
USPC ................................................ 106/3; 510/180
See application file for complete search history.

(56) References Cited

U.S. PATENT DOCUMENTS

| | | | | |
|---|---|---|---|---|
| 2,746,875 | A * | 5/1956 | Mills ........................ | C09G 1/08 106/272 |
| 4,990,377 | A * | 2/1991 | Wilson ................ | C04B 41/4922 106/2 |
| 5,449,712 | A * | 9/1995 | Gierke ................ | C04B 41/4961 106/2 |
| 8,932,632 | B2 * | 1/2015 | Yadav ..................... | C03C 27/10 156/284 |
| 2007/0237901 | A1 * | 10/2007 | Moses .................... | A01N 55/00 427/384 |

(Continued)

*Primary Examiner* — Gregory E Webb
(74) *Attorney, Agent, or Firm* — Venjuris PC

(57) ABSTRACT

Compositions and methods for making and using the compositions for maintaining clean surfaces are disclosed herein. A preferred composition for maintaining clean surfaces is an aqueous solution that comprises water, silicon dioxide, stearic acid, nitrous oxide, hydrogen and a hydrophobic substance. A preferred hydrophobic substance for this preferred composition is a water soluble powder of Polysilsesquioxane Steardimonium Chloride. A preferred method of making such a composition includes the steps of mixing the solid ingredients—silicon dioxide, stearic acid, and the hydrophobic substance, and then mixing the solid ingredients with water until the ingredients are preferably evenly distributed in the solution at preferably a PH of 0-5. A preferred method of using such a composition includes the steps of applying an even layer of the composition onto a surface and allowing the surface to dry.

7 Claims, 6 Drawing Sheets

| Ingredient | Preferred Weight or Percentage | Preferred Brand/Product |
|---|---|---|
| Pure Water | 97-99 | N/A |
| Silicon Dioxide | .1-2 | N/A |
| Nitrous oxide | .1-.25 | N/A |
| Hydrogen | .1-.2 | N/A |
| Stearic Acid | ph 0-5 | N/A |
| Hydrophobic Substance | .1-2 | SiQuebe Q1850 Substance |
| Total: | 100% | |

(56) References Cited

U.S. PATENT DOCUMENTS

| | | | | |
|---|---|---|---|---|
| 2009/0069270 A1* | 3/2009 | McMahon | ................ | C07F 7/20 514/63 |
| 2010/0239679 A1* | 9/2010 | Greene | ................. | A01N 25/26 424/490 |
| 2015/0203408 A1* | 7/2015 | Sroka | ..................... | C04B 28/02 106/2 |

\* cited by examiner

| Ingredient | Preferred Weight or Percentage | Preferred Brand/Product |
|---|---|---|
| Pure Water | 97-99 | N/A |
| Silicon Dioxide | .1-2 | N/A |
| Nitrous oxide | .1-.25 | N/A |
| Hydrogen | .1-2 | N/A |
| Stearic Acid | ph 0-5 | N/A |
| Hydrophobic Substance | .1-2 | SiQuebe Q1850 Substance |
| Total: | 100% | |

FOOD SERVICE TESTING RESULTS: TUSCON, AZ

| | Baseline Untreated ||||||||
|---|---|---|---|---|---|---|---|---|
| | December 4, 2017 || December 11, 2017 || December 17, 2017 || December 27, 2017 ||
| Location | Pre-Clean | Post-Clean | Pre-Clean | Post-Clean | Pre-Clean | Post-Clean | Pre-Clean | Post-Clean |
| Belt 1 | 28 | 4 | 40 | 1 | 37 | 2 | 40 | 1 |
| Belt 2 | 30 | 3 | 13 | 0 | 50 | 0 | 31 | 0 |
| Belt 3 | 20 | 3 | 75 | 7 | 41 | 0 | 39 | 1 |
| Sizer | 12 | 3 | 25 | 3 | 39 | 3 | 26 | 2 |
| Sort Table | 39 | 3 | 51 | 3 | 39 | 4 | 29 | 0 |
| Bucket Elevator | 100 | 1 | 80 | 2 | 96 | 3 | 81 | 2 |
| Roast Tray | 25 | 0 | 15 | 0 | 21 | 3 | 14 | 0 |
| Totals | 254 | 18 | 299 | 16 | 323 | 15 | 262 | 6 |

| | Baseline Treated ||||||||
|---|---|---|---|---|---|---|---|---|
| | January 2, 2017 || January 8, 2017 || January 15, 2017 || January 22, 2017 ||
| Location | Pre-Clean | Post-Clean | Pre-Clean | Post-Clean | Pre-Clean | Post-Clean | Pre-Clean | Post-Clean |
| Belt 1 | 7 | 0 | 8 | 1 | 6 | 2 | 3 | 0 |
| Belt 2 | 1 | 0 | 1 | 0 | 2 | 0 | 1 | 0 |
| Belt 3 | 7 | 1 | 8 | 3 | 11 | 1 | 12 | 3 |
| Sizer | 8 | 1 | 5 | 3 | 1 | 0 | 1 | 1 |
| Sort Table | 1 | 2 | 1 | 3 | 0 | 0 | 1 | 0 |
| Bucket Elevator | 10 | 1 | 10 | 3 | 5 | 3 | 10 | 1 |
| Roast Tray | 1 | 0 | 1 | 0 | 1 | 0 | 3 | 0 |
| Totals | 35 | 5 | 34 | 13 | 26 | 6 | 31 | 4 |

FIGURES 4A and 4B

HEALTHCARE TESTING RESULTS

SITE 1 RESULTS: HOUSTON, TX

| | 5-week test with one application of GR-AD Pro |||||
|---|---|---|---|---|---|
| Patient Restroom | Feb 3 ATP | Feb 9 ATP | Feb 18 ATP | Feb 24 ATP | Mar 2 ATP |
| RR Door Knob | 1 | 2 | 12 | 2 | 1 |
| Sink Handle | 1 | 1 | 8 | 0 | 2 |
| Toilet Handle | 4 | 3 | 4 | 0 | 18 |
| Handrails | 4 | 1 | 2 | 0 | 1 |
| Light Switch | 5 | 2 | 11 | 3 | 1 |

SITE 2 RESULTS: MERIDEN, CT

| | 5-week test with one application of GR-AD Pro |||||
|---|---|---|---|---|---|
| Patient Restroom | Jan 30 ATP | Feb 10 ATP | Feb 24 ATP | Mar 3 ATP | Mar 10 ATP |
| RR Door Knob | 0 | 4 | 3 | 2 | 10 |
| Sink Handle | 0 | 1 | 12 | 4 | 5 |
| Toilet Handle | 0 | 40 | 10 | 4 | 15 |
| Handrails | 2 | 2 | 33 | 12 | 4 |
| Light Switch | 5 | 30 | 7 | 71 | 10 |
| Soap Dispenser | 4 | 1 | 3 | 38 | 5 |

SITE 3 RESULTS: TULSA, OK

| | 4-week test with one application of GR-AD Pro |||||||
|---|---|---|---|---|---|---|---|---|
| Patient Restroom | Nov 7 Pre-ATP | Nov 7 Post-ATP | Nov 13 Pre-ATP | Nov 13 Post-ATP | Nov 20 Pre-ATP | Nov 20 Post-ATP | Nov 27 Pre-ATP | Nov 27 Post-ATP |
| Lightswitch | 28 | 0 | 33 | 3 | 29 | 5 | 48 | 16 |
| Room Door Knob | 3 | 1 | 7 | 2 | 7 | 2 | 12 | 4 |
| RR Handrail | 4 | 1 | 8 | 1 | 1 | 4 | 12 | 2 |
| Sink Handle | 0 | 0 | 4 | 3 | 15 | 5 | 21 | 3 |
| Toilet Handle | 1 | 0 | 3 | 1 | 0 | 0 | 36 | 12 |
| Overall | 7 | 0 | 11 | 3 | 10 | 2 | 26 | 7 |

| | 4-week test: Control Group |||||||
|---|---|---|---|---|---|---|---|---|
| Patient Restroom | Nov 7 Pre-ATP | Nov 7 Post-ATP | Nov 13 Pre-ATP | Nov 13 Post-ATP | Nov 20 Pre-ATP | Nov 20 Post-ATP | Nov 27 Pre-ATP | Nov 27 Post-ATP |
| Lightswitch | 12 | 0 | 17 | 3 | 32 | 5 | 34 | 14 |
| Room Door Knob | 1 | 0 | 8 | 1 | 3 | 5 | 8 | 2 |
| RR Handrail | 100 | 3 | 60 | 10 | 8 | 14 | 7 | 2 |
| Sink Handle | 7 | 2 | 30 | 1 | 15 | 10 | 3 | 8 |
| Toilet Handle | 20 | 4 | 72 | 1 | 5 | 3 | 1 | 1 |
| Overall | 13 | 2 | 13 | 3 | 14 | 8 | 11 | 5 |

FIGURE 5

Formulation was analyzed via plating for microbials with the following results:

Total Aerobic Count: 0    Total Coliforms: 0
Total Yeast/Mold: 0       Salmonella: 0
Enterobacteriaceae: 0     E. i: 0

Formualtion was diluted 1:100 and analyzed via GC-MS/MS and LC-MS/MS for pesticides. None of the following pesticides were identi-fied in formualtion.

| PESTICIDE/GROWTH REGULATOR (pesticide) | Finding (ppm) | Limits (ppm) | PESTICIDE/GROWTH REGULATOR (pesticide) | Finding (ppm) | Limits (ppm) |
|---|---|---|---|---|---|
| Abamectin | 0 | 0.05 | Fludioxonil | 0 | 0.02 |
| Acequinocyl | 0 | 4 | Imidacloprid | 0 | 0.05 |
| Bifenazate | 0 | 15 | Myclobutanil | 0 | 9 |
| Bifenthrin | 0 | 0.05 | Paclobutrazol | 0 | 0.05 |
| Captan | 0 | 0.05 | Quintozene | 0 | 0.2 |
| Cyfluthrin | 0 | 4 | Piperonyl Butoxide | 0 | 2 |
| Cypermethrin | 0 | 0.05 | Pyrethrin | 0 | 1 |
| Daminozide | 0 | 0.05 | Spinetoram | 0 | 1.7 |
| Dimethomorph | 0 | 60 | Spinosad | 0 | 1.7 |
| Etoxazole | 0 | 7 | Spirotetramat | 0 | 10 |
| Fenhexamid | 0 | 30 | Thiamethoxam | 0 | 0.02 |
| Flonicamid | 0 | 7 | Trifloxystrobin | 0 | 11 |

ABRASION STUDY

COMPOSITIONS FOR MAINTAINING CLEAN SURFACES AND METHODS FOR MAKING AND USING CLEAN SURFACE TECHNOLOGY

BACKGROUND

Disinfectants are widely used in contemporary hospitals, laboratories, water treatment facilities, food service facilities and households to destroy microorganisms that might cause diseases or pollute the environment. Many existing sanitizing and disinfecting products, such as wipes or sprays, comprise chemical solutions that are designed to kill infectious microorganisms, such as bacteria, viruses, fungi, algae, mold, yeast, spores, and so forth. These products are generally limited in that they kill germs only when wet, thus proving no protection after the solutions dry, while requiring a long contact time, such as 30 seconds for chlorine-based products, 10 minutes for quats (quaternary ammonium compounds) based products, and 5 minutes for hydrogen peroxide, before the microorganisms are killed. Some of these products even leave residues that build up on the surfaces applied and are hard to clean.

Additionally, most of the chemical disinfecting products are effective only on certain types of surfaces—e.g., chlorine-based disinfecting products may damage unpainted wood, plastic, or metal surfaces, discolor fabrics, and causes skin irritation while alcohol-based disinfecting products can damage rubber and certain plastic equipment after prolonged uses. Furthermore, these products often cause adaptive organisms that eventually become resistant to the disinfectants.

Even the non-chemical sanitizing and disinfecting technologies, such as ultraviolet (UV) germicidal radiation, dry heat, and autoclaving, have their limitations. For instance, similar to the chemical disinfecting products, these technologies do not have any lasting germ-killing effects after the disinfecting process is done. Additionally, UV radiation may kill germs on smooth surfaces but does not work on porous surfaces, such as wood or foam, because of its weak penetrating ability. Dry heat and autoclaving that sterilizes with steam are limited to disinfecting only heat-resistant objects. Additionally, the exposure time needed for these methods is generally long; e.g., at least 10 minutes for UV radiation, an hour for dry heat, and at least 4 minutes for pre-vacuum autoclaving. Furthermore, exposure to these methods are not safe for operators—all can damage skin and eyes.

In order to solve the issue of short effective time of disinfecting products, surface coating technologies are developed for maintaining a clean, disinfected surface. Existing clean surface technologies provide products with antimicrobial agents that are generally either silver-based or triclosan-based and designed to leach out into the surface. When the surface these products applied to is human skin, studies show that these products may release ionic free radicals or organic radicals that could react with, or be metabolized by, cells. Additionally, like many disinfecting products, these surface coatings tend to cause the development of adaptive organisms, and thus their antimicrobial effects reduce over time.

It is thus desirous to have a non-toxic, safe product or method that prepares a germ-inhabitable surface, including the skin, and makes the microorganisms on the surface to be easily removed by cleaning or shaking or effectively killed by disinfecting products.

It is also desirous to have a product or method that keeps a surface clean, germ-free for a sufficiently long time and thus reduces the frequency of the routine cleaning protocols required.

Finally, it is desirous to have a product or method that does not leach into a surface or create or promote any adaptive organisms.

SUMMARY

The structure, overall operation and technical characteristics of the present invention will become apparent with the detailed description of preferred embodiments and the illustration of the related drawings as follows.

This invention is embodied in compositions for maintaining clean surfaces and methods for making and using such compositions. An exemplary composition is an aqueous solution that comprises water, silicon dioxide, stearic acid, nitrous oxide, hydrogen, and a hydrophobic substance. In a preferred embodiment, the hydrophobic substance is a water soluble powder product by Gelest Inc., with a product code of SiQuebe™ Q1850, and an INCI (International Nomenclature of Cosmetic Ingredients) name of Polysilsesquioxane Steardimonium Chloride (referred to as "SiQuebe Q1850 Substance"). While other weight percentage are effective, in a preferred embodiment, the preferred solution may comprise, by weight, 97%-99% water, 1%-2% silicon dioxide, 0.5%-1% nitrous oxide, 0.25%-1% Siqube 0.25%-2% With a PH of 0-5 and various mixtures thereof.

Various embodiments may adopt different substitute ingredients. In an alternate embodiment water can be substituted for isopropanol, ethanol, or ethylene glycol as the base solution. In another alternative embodiment, the hydrophobic substance can be substituted with Octadecyltriethoxysilane; Triethoxysilyloctadecane or Octadecyltrimethoxysilane; Trimethoxyoctadecylsilane; Trimethoxysilyloctadecanecan.

The preferred composition, as illustrated above, can be effective on animate and/or inanimate surfaces. When this preferred composition with the ingredients evenly distributed therein is applied, either wiped or sprayed, onto a clean surface, the hydrophobic substance becomes chemically bound by polycondensation to the silanol group in the composition and forms a high-molecular-weight polymer while drying. While not being held to any theory, it is believed that the high-molecular-weight polymer of this exemplary composition then turns into a thin residual coating, forming a physical barrier, on the surface that is inhospitable to microorganisms, resistant to abrasion and increases the efficiency of common disinfection. Preferably, the solution is dried at standard room temperatures typically taking 2-3 minutes. In another preferred embodiment, accelerated drying by fans or heat can be used. With this microorganism-inhospitable coating on the surface, germs cannot root on the surface and are thus more vulnerable to disinfecting products.

Furthermore, an embodiment of the composition preferably comprises only GRAS—(Generally Recognized as Safe) compliant ingredients, and are VOC free and thus can be safely used in various environments and/or industries, such as healthcare, schools, hospitals, oil/gas, food service, cosmetics or skin care products, textiles, and so forth. Indeed, the ingredients of the preferred composition, including the silicon dioxide, the stearic acid, nitrous oxide and hydrogen and the preferred hydrophobic substance, the SiQuebe Q1850 Substance, are known to be non-toxic to humans, and even safe for food contact surfaces. Additionally, the preferred composition, as well as its ingredients, are known to be chemically stable, generally do not interact with common surface materials, disinfectants, or other chemicals, and thus would not damage the surface or reduce the effectiveness of disinfecting products. Moreover, since the preferred composition does not itself kill or affect the microorganisms, but rather builds a physical barrier that prevents the microorganisms from contacting the surface, it would not promote any form of adaptations or alterations of the microorganisms.

Finally, experiments and clinical tests have shown that this preferred composition provides an antimicrobial barrier of 99.99% protection for at least 30 days in hospital restrooms. The barrier formed after the preferred composition dries can still be 99.99% effective after the surface coated with the composition being abraded for 1000 times. Also, the preferred composition is stable and tested to have over 3 years of shelf life.

As to making the compositions stated above, an exemplary method includes the following steps:
 Step 1: mixing suitable amounts of, silicon dioxide, stearic acid, nitrous oxide, hydrogen and hydrophobic substance into Phase I;
 Step 2: combining Phase I with a suitable amount of water. The water should be roughly 80 degrees Fahrenheit.
 The PH of the product can be from 0-5
 Step 3: mixing into Phase II until homogeneous; and
 Step 4 (optional): pouring the mixed Phase II into a container for storage.

An exemplary method to create and maintain a clean surface comprises the following steps:
 Step 1: cleaning the surface according to standard cleaning protocols;
 Step 2: applying a composition, that is an evenly-mixed solution with water, silicon dioxide, nitrous oxide, hydrogen, stearic acid, and hydrophobic substance, onto the surface;
 Step 3: allowing the composition dry on the surface; and
 Step 4: determining if a predetermined expiration day (e.g. 30 days, or less if the surface is frequently used) is reached? If so, go back to Step 1.

One object of this invention is to provide a non-toxic, safe composition for maintaining a clean surface that is inhospitable to microorganism and increase the efficiency of common disinfectants for at least 7 days, preferably more than 30 days.

Another object of this invention is to provide a composition for maintaining a clean surface, while no damaging the surface, regardless of the surface's material.

Yet another object of this invention is to provide a composition that does not cause any adaptations or alterations of the microorganisms or affect the effectiveness of the disinfecting products to be used.

Yet another object of this invention is to stabilize a non-toxic formula that is non abrasive in a PH of 0-5.

BRIEF DESCRIPTION OF THE DRAWINGS

FIG. 1 shows the table of a preferred embodiment of the composition for creating and maintaining a clean surface.

FIGS. 3 and 3C shows a flow chart of a preferred method of using an exemplary composition for creating and maintaining a clean surface and test results.

FIGS. 4A-4B depict tables showing the ATP (Adenosine Triphosphate) test results in hospitals with surfaces with only one application of a preferred composition.

FIG. 5 shows a table with the test results of common pesticides in the preferred composition (1:100 diluted), analyzed via GC-MS/MS (Gas Chromatograph—tandem Mass Spectrometer) and LC-MS/MS (Liquid Chromatograph—tandem Mass Spectrometer).

DESCRIPTION OF THE EMBODIMENTS

FIGS. 1-6 show a preferred embodiment of the composition, preferred methods of making and using an embodiment of the composition, and various test results showing the features of the preferred composition. The preferred composition in FIG. 1 comprises preferred weight percentages of water, silicon dioxide, nitrous oxide, hydrogen, stearic acid, and a hydrophobic substance (the SiQuebe Q1850 Substance).

Figure 2:
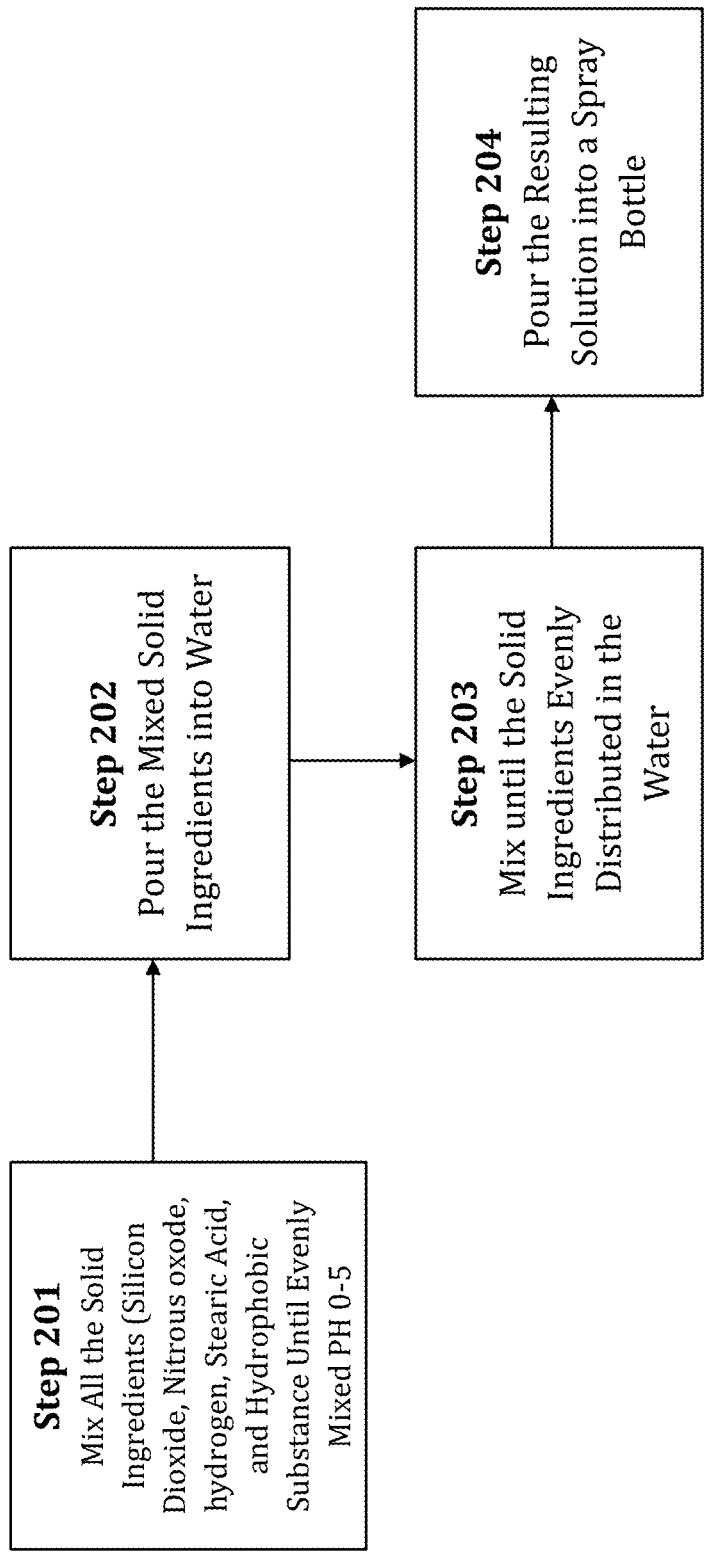
FIG. 2 shows a flow chart of a preferred method of making an exemplary composition for creating and maintaining a clean surface.

FIG. 2 shows a preferred method of making such a composition includes the steps of:
 Step 201: mixing the solid ingredients-1-2 wt. % silicon dioxide, stearic acid of a PH 0-5, and 1-2 wt. % the hydrophobic substance (SiQuebe Q1850 Substance)—into Phase I;
 Step 202: combining Phase I with 97-99 wt. % water at 80 degrees Fahrenheit into Phase II;
 Step 203: mixing Phase II until turning into a homogeneous solution (Phase III);
 Step 204: pouring Phase III into a container (e.g. a bottle with a cap or a spray head or a can with lid) for storage.

Figure 3:
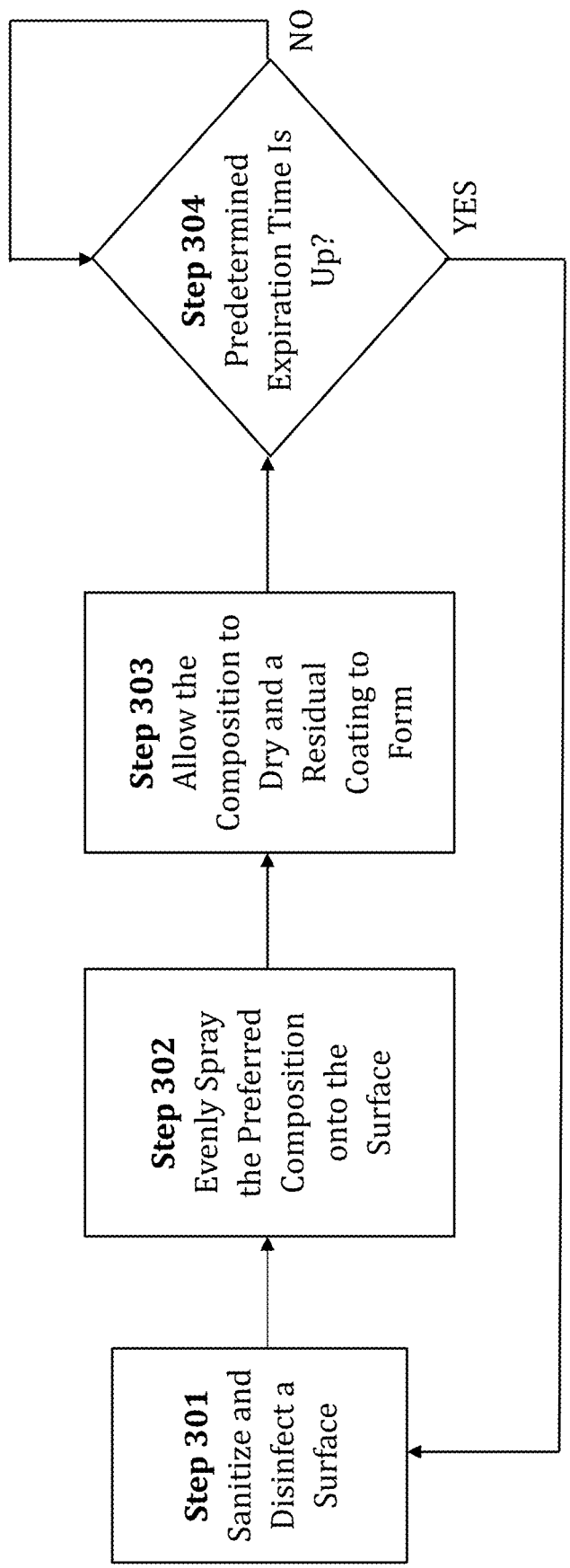

A preferred method of using a composition for creating and maintaining a clean surface is depicted in FIG. 3. The preferred method includes the steps of:
 Step 301: sanitizing and disinfecting a surface;
 Step 302: applying an even layer of an exemplary composition, such as the preferred composition in FIG. 1, onto the surface;
 Step 303: allowing the surface with the composition to dry and a residual coating to form; and
 Step 304: determining if the predetermined expiration time (e.g., 30 days for the preferred composition) is up? If so, go back to Step 301.

Various clinical studies and experiments have been performed to test the preferred composition in FIG. 1. ATP tests were carried out in two hospitals in 2017 in order to test the efficacy of the preferred composition, and the results are shown in FIGS. 4A-4B. ATP testing is known to be effective in monitoring sanitation and thus commonly used in hospitals and the food industry. In these experiments over 5 weeks of time, the preferred composition was applied only once onto the surfaces of the listed objects (including door knobs/handles, sink handles, toilet seats, and so forth), immediately after the surfaces were disinfected and sanitized by the hospitals' standard cleaning protocols. Then the surfaces with the newly applied preferred composition were allowed to dry before the first ATP tests.

An ATP meter, Hygenia SystemSURE ATP monitor, was used in the experiments to measure the ATPs, i.e. the amount of organic materials in a sample, in RLU (Relative Light Units). To determine the amount of ATPs, a sample was obtained by swabbing a surface and then treated with a reagent that illuminates ATPs for the NIP meter to quantify the amount of ATPs in the sample based on the luminescence. Generally a surface with a reading of 0-100 RLU is considered sanitary in a hospital. A reading of 101-200 RLU is marginal, and a surface with a reading over 200 RLU requires immediate cleaning.

As shown in the tables in FIGS. 4A-4B, only one surface (the sink handle in FIG. 4B) had a reading above 100 RLU—39 days after the surface was treated with the preferred composition, without the addition of the current embodied formula. Common standard cleaning protocols were maintained but exemplified and the efficiency of the cleaning protocols amplified were noted. As such, the preferred composition effectively increase the efficiency of daily cleaning by keeping the numbers of microbes on the surfaces sufficiently low for more than 30 days, even in public areas like hospitals.

As shown in the table in FIG. 5, the readings of common pesticides, in the preferred composition in FIG. 1, when diluted by 1:100, determined via GC-MS/MS and LC-MS/MS testing, were consistently zero ppm (parts per million). Therefore, the preferred composition is non-toxic and generally recognized as safe for contact or consumption.

Figures 6A, 6B, 6C:
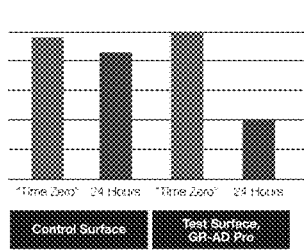
FIGS. 6A, 6B and 6B show tables with the microbes counts in CFU (Colony Forming Units) on two surfaces, one control surface and the other treated of the preferred composition, after 1000 passes of abrasion in 24 hours.

FIGS. 6A-6C show the efficacy of the preferred composition on 2" by 1.5" plastic coupons as the test surfaces were subjected to abrasion. This tests the efficacy of nonporous surfaces, such as plastics, metals, and ceramics—i.e. the ability of these surfaces to maintain safe levels of microorganisms, or increase the efficiency of common disinfectant—by determining the microbial concentrations in the samples.

Half of the plastic coupons in this test experiment were test samples, treated with the preferred composition, and the other half were control samples. Before the experiment, the surfaces of the test samples were subjected to abrasion with a Gardco™ washability and wear tester, where a weight of approximately 450 g was placed on the abrasion track and passed over the surfaces of the coupons for 500 cycles (1000 passes) over the course of approximately 30 minutes. Therefore, the test results indicate that the residual coating of the preferred composition is resistant to abrasion.

While the invention has been described by means of specific embodiments, numerous modifications and variations could be made thereto by those ordinary skilled in the art without departing from the scope and spirit disclosed herein.

Alternate composition comprised of a base solution of isopropanol, ethanol, and ethyl glycol have been substituted for the water phase.

Also maintaining a ph 0-5 with any toxicity, corrosiveness, and nonabrasive has allowed the formula to maintain a high level of efficient cleaning on the surface.

What is claimed is:

1. A composition, having a pH between 0 and 5, for creating and maintaining a clean surface, comprising:
    a. water;
    b. silicon dioxide;
    c. stearic acid; and
    d. a hydrophobic substance;
wherein the hydrophobic substance has solubuility in water in a pH between 0 and 5 and is hydrophobic upon drying.

2. The composition in claim 1, wherein the hydrophobic substance is selected from a list of Polysilsesquioxane Steardimonium Chloride, Octadecyltriethoxysilane; Triethoxysilyloctadecane or Octadecyltrimethoxysilane; Trimethoxyoctadecylsilane; Trimethoxysilyloctadecane and mixtures thereof.

3. The composition in claim 1, wherein the solution weight percentages is selected from the group consisting of:
    a. water; 97%-99%,
    a. silicon dioxide; 1%-2%,
    b. nitrous oxide 0.5%-0.7%,
    c. hydrogen 0.5%-1%,
    d. and a hydrophobic substance 1%-2%, and mixtures thereof
and wherein the steric acid in the composition is sufficient to create a pH between 0 and 5.

4. A method for making a composition for creating and maintaining a clean surface, comprising the steps of:
    a. mixing silicon dioxide, stearic acid, and a hydrophobic substance into Phase I;
    b. combining Phase I with water into Phase II; and
    c. mixing Phase II until turning into a homogeneous solution, Phase III
wherein the hydrophobic substance has solubuility in water in a pH between 0 and 5 and is hydrophobic upon drying.

5. The method in claim 4 further comprises a step of: pouring Phase III into a container for storage.

6. The method in claim 4, wherein the hydrophobic substance is selected from the group consisting of Polysilsesquioxane Steardimonium Chloride, Octadecyltriethoxysilane; Triethoxysilyloctadecane or Octadecyltrimethoxysilane; Trimethoxyoctadecylsilane; Trimethoxysilyloctadecane and mixtures thereof.

7. The method in claim 4, wherein the solution weight percentages is selected from the group consisting of:
    a. water; 97%-99%
    b. silicon dioxide; 1%-2%
    c. nitrous oxide 0.5%-0.7%
    d. hydrogen 0.5%-1%
    e. and a hydrophobic substance 1%-2%
    and wherein the stearic acid in the composition is sufficient to create a pH between 0 and 5.

* * * * *